(12) United States Patent
Fukunaga et al.

(10) Patent No.: US 9,265,863 B2
(45) Date of Patent: Feb. 23, 2016

(54) M CELLS AND ARTIFICIAL SKIN SHEET

(71) Applicants: Hajime Fukunaga, Ube (JP); Dennis Kopecko, Silver Spring, MD (US)

(72) Inventors: Hajime Fukunaga, Ube (JP); Dennis Kopecko, Silver Spring, MD (US)

( * ) Notice: Subject to any disclaimer, the term of this patent is extended or adjusted under 35 U.S.C. 154(b) by 0 days.

(21) Appl. No.: 14/438,515

(22) PCT Filed: Apr. 4, 2013

(86) PCT No.: PCT/JP2013/060312
§ 371 (c)(1),
(2) Date: Apr. 24, 2015

(87) PCT Pub. No.: WO2014/064951
PCT Pub. Date: May 1, 2014

(65) Prior Publication Data
US 2015/0273115 A1    Oct. 1, 2015

(30) Foreign Application Priority Data

Oct. 25, 2012  (JP) ................................ 2012-235293

(51) Int. Cl.
*C12N 5/071* (2010.01)
*A61L 27/60* (2006.01)
*A61L 27/38* (2006.01)
*A61L 27/54* (2006.01)
*A61F 2/10* (2006.01)

(52) U.S. Cl.
CPC ................ *A61L 27/60* (2013.01); *A61F 2/105* (2013.01); *A61L 27/3804* (2013.01); *A61L 27/54* (2013.01); *C12N 5/0698* (2013.01); *A61L 2300/252* (2013.01); *A61L 2300/41* (2013.01); *A61L 2300/426* (2013.01)

(58) Field of Classification Search
IPC ....................................... C12N 5/0698,2506/23
See application file for complete search history.

(56) References Cited

FOREIGN PATENT DOCUMENTS

JP    2008-141995 A    6/2008
WO    2012077811 A    6/2012

OTHER PUBLICATIONS

Pielage et al., "Reversible differentiation of Caco-2 cells reveals galectin-9 as a surface marker molecule for human follicle-associated epithelia and M cell-like cells," The International Journal of Biochemistry and Cell Biology 39:1886-1901, 2007.*
International Search Report in PCT/JP2013/060312 dated May 7, 2013.
Hiroshi Ono, "Biology of M cells, a unique subset of intestinal epithelial cells", Journal of Japanese Biochemical Society, 2011, 83 (1), pp. 13 to 22, International Search Report label of "A" only; Examiner cannot read Japanese; no English translation provided.
Takako Wada, "Jusho Necchushorei to Skin Bank• Hifu Baiyo", The Japanese Journal of Artificial Organs, 2008, 37 (1), pp. 67 to 75, International Search Report label of "A" only; Examiner cannot read Japanese; no English translation provided.

* cited by examiner

*Primary Examiner* — Rosanne Kosson
(74) *Attorney, Agent, or Firm* — Global IP Counselors, LLP

(57) ABSTRACT

[Problem] To provide M cells having excellent strength and anti-allergy activity and an artificial skin sheet formed from the M cells. [Solution] GP2 contained in the M cells is transferred to the intracellular tight junction and galectin 9 is expressed in the M cells. Moreover, a structure is formed in which both GP2 and galectin 9 are present at the M cell surface.

2 Claims, 13 Drawing Sheets
(13 of 13 Drawing Sheet(s) Filed in Color)

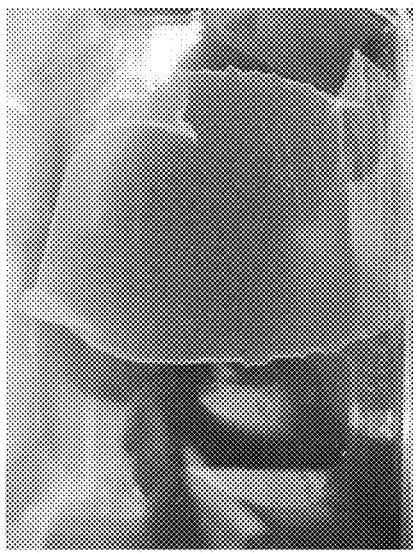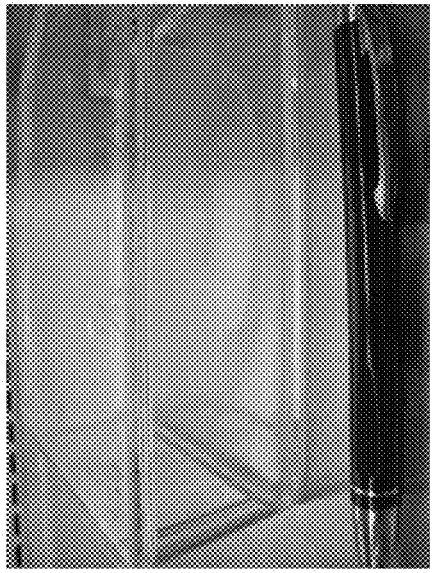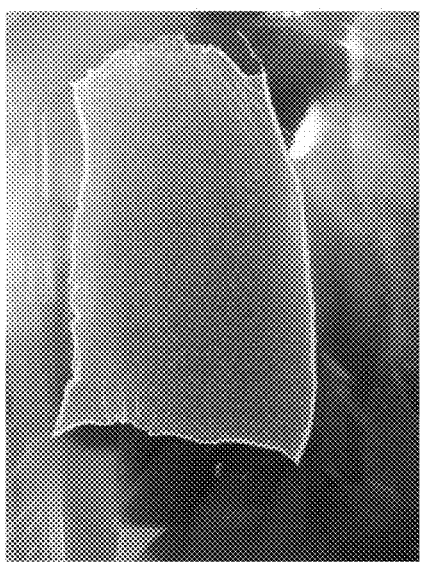
FIG. 7

FIG. 12  Binding assay with Galectin-9 on GP2 ELISA plate

M CELLS AND ARTIFICIAL SKIN SHEET

CROSS-REFERENCE TO RELATED APPLICATIONS

This application is a U.S. National stage application of International Application No. PCT/JP2013060312, filed Apr. 4, 2013, which claims priority under 35 U.S.C. §119(a) to Japanese Patent Application No. 2012-235293 filed in Japan on Oct. 25, 2012. The entire contents of Japanese Patent Application No. 2012-235293 are incorporated by reference herein.

BACKGROUND

1. Field of the Invention

The present invention relates to M cells and an artificial skin sheet having excellent cell adhesiveness and anti-allergy activity.

2. Background Information

An artificial skin has been conventionally used after a severe burn, damage to the skin caused by accident, and a resection of a tumor such as skin cancer, or for a cleft lip, a cleft palate and such. A typical artificial skin is primary composed of collagen taken from dermis and tendons of cows and pigs.

After washing a wound thoroughly and removing unnecessary tissues, patching an artificial skin with a thread and such, and fixing it by pressing lightly is how to use the artificial skin. Then fibroblasts, which become capillaries and cells, penetrate into artificial skin sponges from subcutaneous tissues, and become close to the state of the original skin in two to three weeks.

Problems of the aforementioned conventional artificial skin are that there is little perspiration and hair growth from the patched area, it feels inferior, and it may darken. Thus, a hair transplant or a hairpiece is needed for areas such as the scalp.

The article "Severe Burn Cases and Skin Bank•Cultured Skin Artificial Organs Volume 37-1, 2008" has disclosed that an allogeneic skin (other person's skin), an artificial skin, and a dermal substitute are used as a treatment of a severe burn. This article has also disclosed that a cultured skin which proliferates cells as an example of the artificial skin.

Additionally, for the artificial skin composed of the cultured skin, 3T3-J2 cells are conventionally used to create a favorable culture environment.

While it is not directly related to the artificial skin, Japanese Patent Application Publication No. 2008-141995 has proposed that GP2 is specifically expressed in M cells (Microfold cells), especially in human M cells, and the GP 2 is used as a marker cell for M cells.

Here, M cells are scattered between absorptive epithelial cells of a follicle-associated epithelium covering Peyer patches, have a film form without microvilli, and capture bacteria and viruses. Also, GP2 is a glycoprotein expressed specifically in M cells, and it is reported that GP2 takes in enteric microbes as an endocytosis receptor.

Similarly, while it is not directly related to the artificial skin, International Patent Application Publication No. WO2012077811 has disclosed that galectin-9 has a function to act on immune cells, and to suppress an excessive inflammation by regulating immunity in the direction of suppression.

SUMMARY

Although the article "Severe Burn Cases and Skin Bank•Cultured Skin Artificial Organs Volume 37-1, 2008" introduces types of artificial skin, it has yet to propose an artificial skin effective for atopic dermatitis. It is supposed that atopic dermatitis is triggered by the following four causes overlapping each other. Namely, (1) a constitutional predisposition which easily has inflammation; (2) a thin skin which easily allows allergens to enter; (3) histamine is abnormally secreted in reaction to an allergen; and (4) a globulin immune antibody is abnormally secreted.

Out of the above-mentioned causes, cause (2) can be eliminated by strengthening and thickening skin itself.

There have been many reports that symptoms of atopic dermatitis get worse by allergens entering into skin. By contrast, while one may have a constitutional predisposition to atopic dermatitis, there are many cases where no symptoms of atopic dermatitis are displayed when one's skin is strong, because no allergen can enter from the skin.

The outermost layer of skin is the stratum corneum which functions as a barrier, but a patient with atopic dermatitis secretes only a small amount of EPA and hyaluronic acid, which leads to thinning of the stratum corneum, allows allergens to enter from the skin, and causes the skin conditions to worsen. In other words, conventional artificial skin has problems that the intercellular connection is weak, and allergens adhering to the surface and allergens entering into the skin cannot be removed.

On the other hand, Japanese Patent Application Publication No. 2008-141995 has been aware that the GP2 is expressed specifically in the M cells; however, it has yet to associate this awareness with any improvement of the artificial skin.

Similarly, International Patent Application Publication No. WO2012077811 has been aware that the galectin-9 has a function to act on immune cells, and to suppress an excessive inflammation by regulating immunity in the direction of suppression; however, it has yet to associate this awareness with any improvement of the artificial skin.

Additionally, neither Japanese Patent Application Publication No. 2008-141995 nor International Patent Application Publication No. WO2012077811 mentions any connection between the GP2 and the galectin-9.

The present inventors have achieved the present invention based on the acquired knowledge that a sheet forming capability is exhibited by moving the GP2 in the M cells to tight junctions, and the galectin-9 which connects with allergens and bacteria is simultaneously expressed in the M cells.

Further, the present inventors have achieved the present invention by examining the relation between the GP2 and the galectin-9, and acquiring knowledge that a new structure is formed by coexistence of the GP2 and the galectin-9, and as a result of this structure, bacteria (allergens) are easy to be captured in the M cells.

Here, a tight junction refers to an area connecting between cells which make up the stratum granulosum under the stratum corneum. When the tight junction is weak, moisture will leak from cells, and a form such as a sheet-form cannot be maintained.

Namely, the artificial skin sheet according to the present invention includes the M cells. In the artificial skin sheet according to the present invention, a part of the GP2 contained in the M cells is moved to the intercellular tight junction, and the galectin-9 is expressed in the M cells.

Here, the aforementioned M cells can be extracted or developed, for instance, from Caco-2 cells. The M cells which exist in cecum lymphoid follicles, large intestine lymphoid follicles and such are also acceptable.

The artificial skin sheet according to the present invention has the GP2 in the area of tight junctions, which strengthens an intercellular connection, thus can create a sheet-like form, and makes it more difficult for allergens to enter paracellulary through the cells from the tight junctions.

Further, galectin-9 is expressed in the M cells which constitute the artificial skin sheet according to the present invention. This galectin-9 forms a special structure with the GP2, captures foreign objects such as bacteria and allergens close to the surface of the M cells, and takes the foreign objects in the cells. In the process of passing through the cells, the galectin-9 adheres to such foreign objects.

Moreover, while the galectin-9-binding bacteria and allergens which have passed through the M cells are phagocytized by dendritic cells (DC cells) as immune cells, an excessive immune response can be suppressed by the immune suppressing function of galectin-9.

In addition, galectin-9 stabilizes mast cells, and suppresses inflammation by inhibiting the mast cells from excessively releasing histamine.

Therefore, the artificial skin sheet according to the present invention has an excellent physical characteristic of skin, that is, a sheet-like form as well as excellent strength. The artificial skin sheet according to the present invention also has high resistivity against bacteria and allergens. Since skin is a boundary area with an external environment, skin is always exposed to infection from bacteria and such which are present in the environment. In particular, treatment of skin damage such as burns and atopic dermatitis requires attention to infection. By using the M cells according to the present invention, treatment without antibiotics and steroids becomes possible.

Since the artificial skin sheet according to the present invention is made of single cells (M cells), the size of the artificial skin sheet can be freely modified, and the artificial skin sheet can be freely set up for an adult or a child, or in accordance with the size of the treatment area.

Also, the M cells which constitute the artificial skin sheet according to the present invention have been confirmed to have a non-deteriorated capacity of producing GP2 and galectin-9 even when the cultivation is resumed after being frozen and stored for over a year.

Therefore, the M cells can be frozen in advance and cultured when necessary, so that a free-sized cell sheet can be provided. The M cells according to the present invention have the potential for usage in all humans.

In addition, as disclosed in the article "Severe Burn Cases and Skin Bank•Cultured Skin Artificial Organs Volume 37-1, 2008", immunorejection does not occur with the cultured skin. Since galectin-9 has a function of suppressing immunity, the present invention is further beneficial. Moreover, in the immune study, the cultural environment useful for the analysis of the immune reaction can be provided by culturing these cell sheets on top of a filter of Transwell™ which is capable of creating apical and basolateral cultural environments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Referring now to the attached drawings which form a part of this original disclosure.

FIG. 7 is a photograph which shows a state during cultivation.

DETAILED DESCRIPTION OF THE EMBODIMENTS

In an embodiment, CaCo-2 cells were selected as cells containing M cells. The CaCo-2 cells were stimulated by antibodies of cytokine receptors (LTβR). With a continuous stimulation, GP2 was continuously expressed. Also, with the continuous stimulation, cells capable of taking in viruses and bacteria or particles appeared.

For the purpose of specifically selecting the aforementioned cells which are capable of taking in viruses and bacteria, the cultured cells were infected with a virus which expresses a fluorescent substance. Because of their phagocytosis capability, the cells infected with the virus express fluorescence, and cells which emit fluorescence were sorted by a cell sorter.

The above procedure was repeated until the cells (the M cells) which expressed GP2 became 99.9% of total.

Figure 1A:
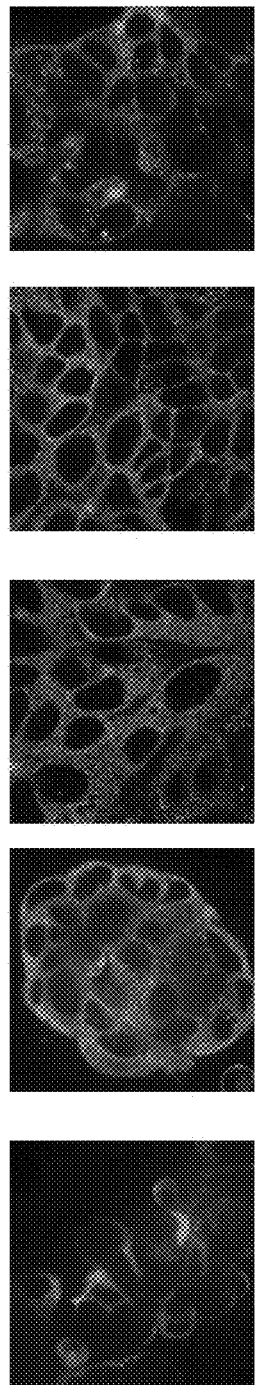
FIG. 1A is a fluorescence microscopy photograph (without LTβR antibodystimulation) showing the relation over time between the cells constituting the artificial skin sheet according to the present invention and the expression of GP2.
Figure 1B:
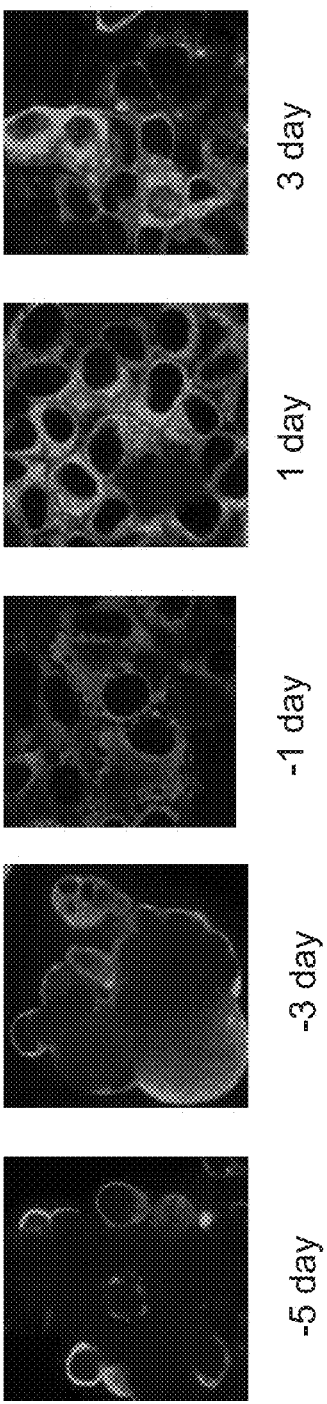
FIG. 1B is a fluorescence microscopy photograph (without LTβR antibody stimulation) showing the relation over time between the cells constituting the artificial skin sheet according to the present invention and the expression of galectin-9.

FIGS. 1A and 1B are microscope photographs showing the sequentially observed results of the expression of the GP2 and the galectin-9 without LTβR antibody stimulation. The annotation "1 day" in the figures refers to the day when the M cells formed a complete sheet, while other dates indicate how many days have passed from "1 day", which is a reference date.

Figure 2:
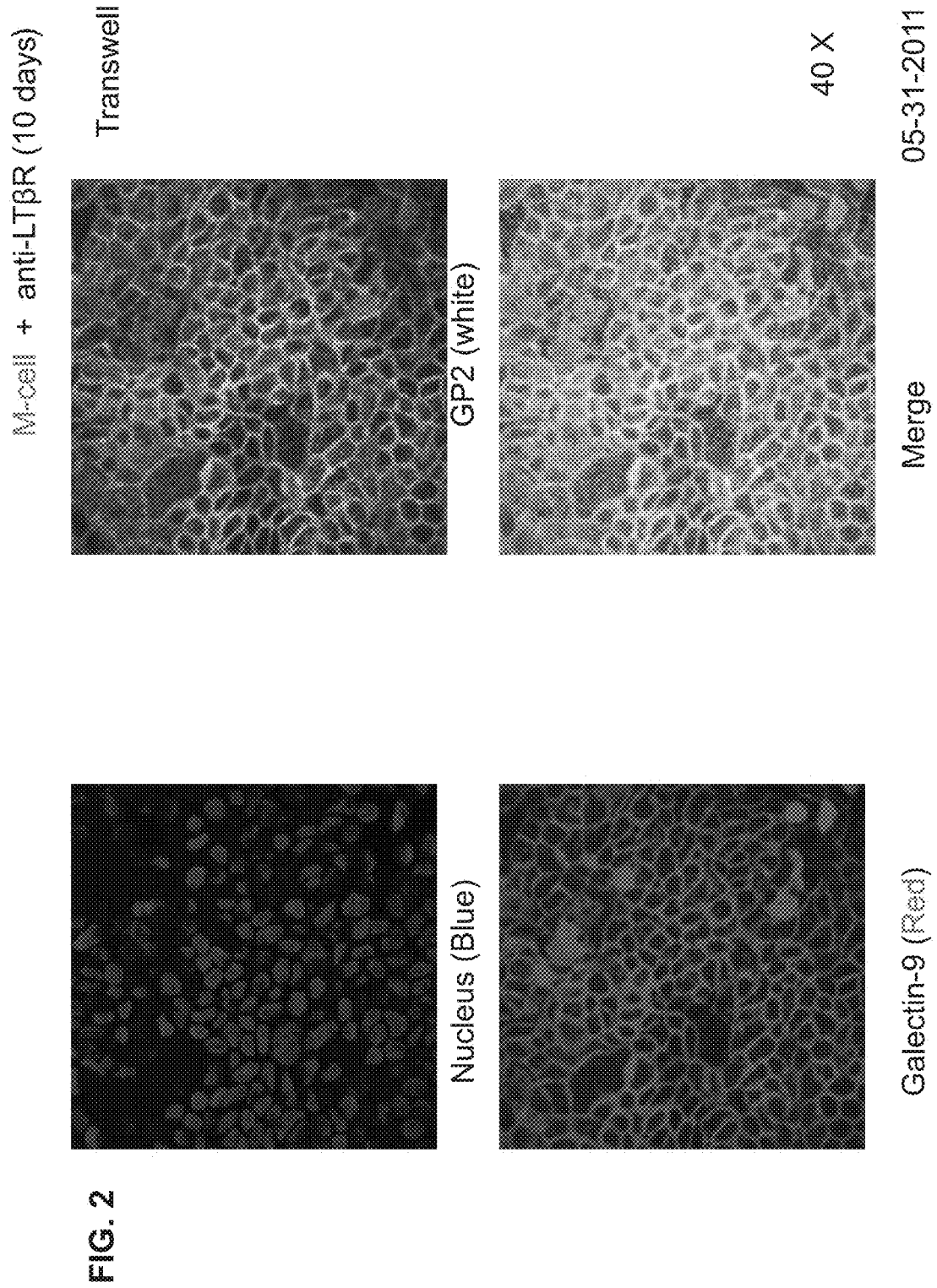
FIG. 2 is a photograph of observation with a confocal microscope when the LTβR antibodies are acted on the M cells.

FIG. 2 shows photographs of the M cells stimulated by LTβR antibodies and observed with a confocal microscope. The upper left photograph shows a state in which each cell is stained with blue, without staining either the GP2 or the galectin-9. The upper right photograph shows a state in which the GP2 is caused to emit light with white fluorescence. The lower left photograph shows a state in which the galectin-9 is caused to emit light with red fluorescence. The lower right photograph shows a state in which the GP2 and the galectin-9 are caused to emit light simultaneously.

The upper right and lower left photographs show that GP2 gathers in the intercellular tight junctions.

Figure 3:
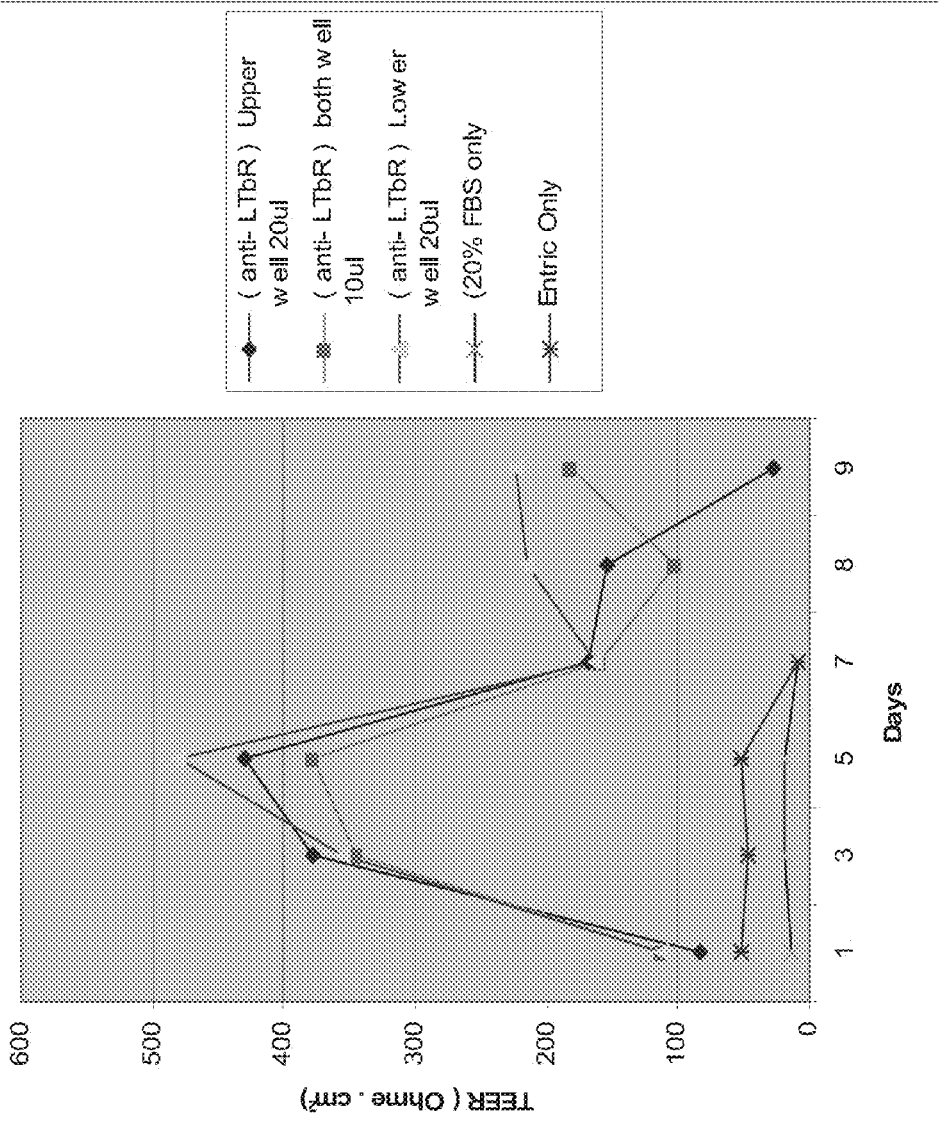
FIG. 3 is a graph showing the measurement results of the degree of intercellular binding using a transepithelial electrical resistance method (TEER).

FIG. 3 is a graph showing the measurement results of the degree of intercellular binding, with the use of a transepithelial electrical resistance method (TEER). The day when the cells have become a complete sheet is set as the day one, and the numbers on the horizontal axis show the number of days lapsed subsequently.

The LTβR antibodies were replaced with new ones every two days, and the electrical resistance was measured each time. The M cells were cultured in a cultivation container (Transwell), which allows the measurement of electrical resistance. Experiments were performed respectively in a case in which 20 μl of antibodies were added to the upper part of the cultivation container, in a case in which 20 μl of antibodies were added to both the upper and lower parts of the cultivation container, in a case in which 20 μl of antibodies were added to the lower part of the cultivation container, in a case in which only a 20% serum culture solution was contained, and in a case in which only a serum-free culture solution was contained.

As a result, it is observed that the resistance value barely changed in the cases in which only the 20% serum culture solution was contained and only the serum-free culture solution was contained, while the resistance value dramatically increased and continued to increase further in the case in which the LTβR antibodies were added to the lower part of the cultivation container. It is observed also from this data that GP2 has been moved to the tight junctions.

Figure 4A:
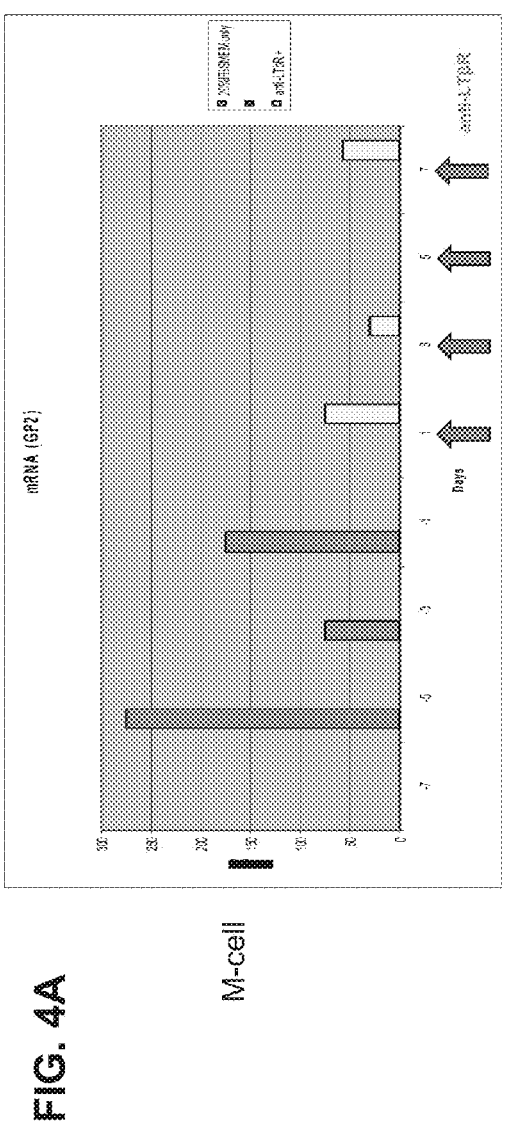
FIG. 4A is a graph showing the measurement results of mRNA of the GP2, which was performed concurrently with the TEER experiments.
Figure 4B:
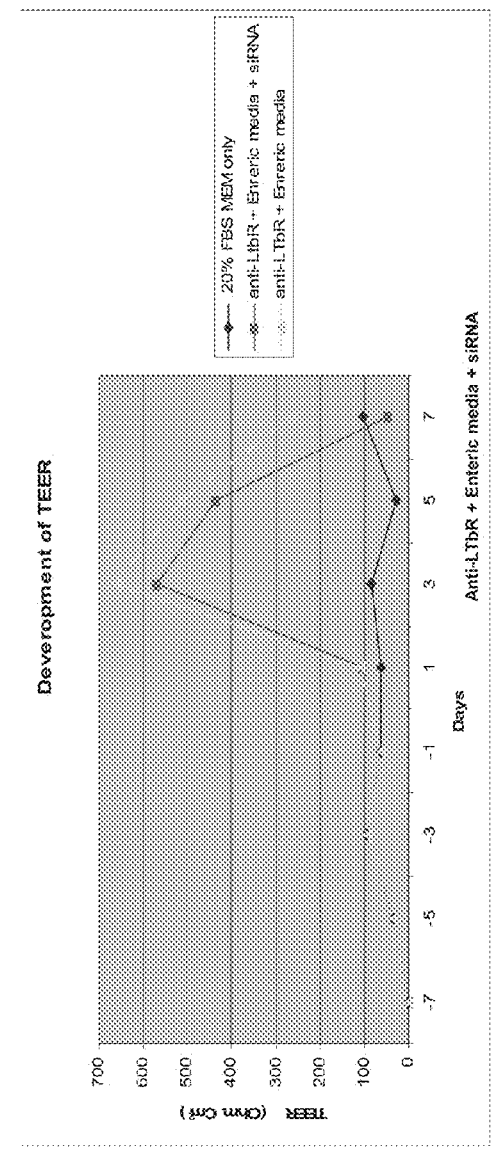
FIG. 4B is a graph showing the measurement results by the TEER method of the cells to which siRNA was added.

FIG. 4A is a graph showing the measurement results of mRNA of GP2, which was performed concurrently with the TEER experiments, and FIG. 4B is a graph showing the measurement results by the TEER method of the cells to which siRNA was added. In FIG. 4A, the mRNA (messenger RNA) for GP2 gradually decreased as the cultivation progressed, and could not be detected at the point when the cells became a sheet form (a blue arrow). However, the mRNA of GP2 (a yellow bar) was detected again when LTβR antibodies were added from Day 1.

FIG. 4B shows the experimental results of TEER in a case in which LTβR antibodies were added in the cultivation container, in a case in which LTβR antibodies and siRNA were added in the cultivation container, and in a case in which only a 20% serum culture solution was contained. The experimental results show that the mRNA is suppressed by the siRNA, and GP2 protein synthesis decreases. Also, it is observed that when the GP2 protein synthesis decreases, the TEER value goes down and the binding strength is deteriorated.

As for galectin-9, it is also observed from FIG. 1B that the amount of expression inside cells increases (shown in deep green) as time passes.

Figures 5A, 5B, 5C:
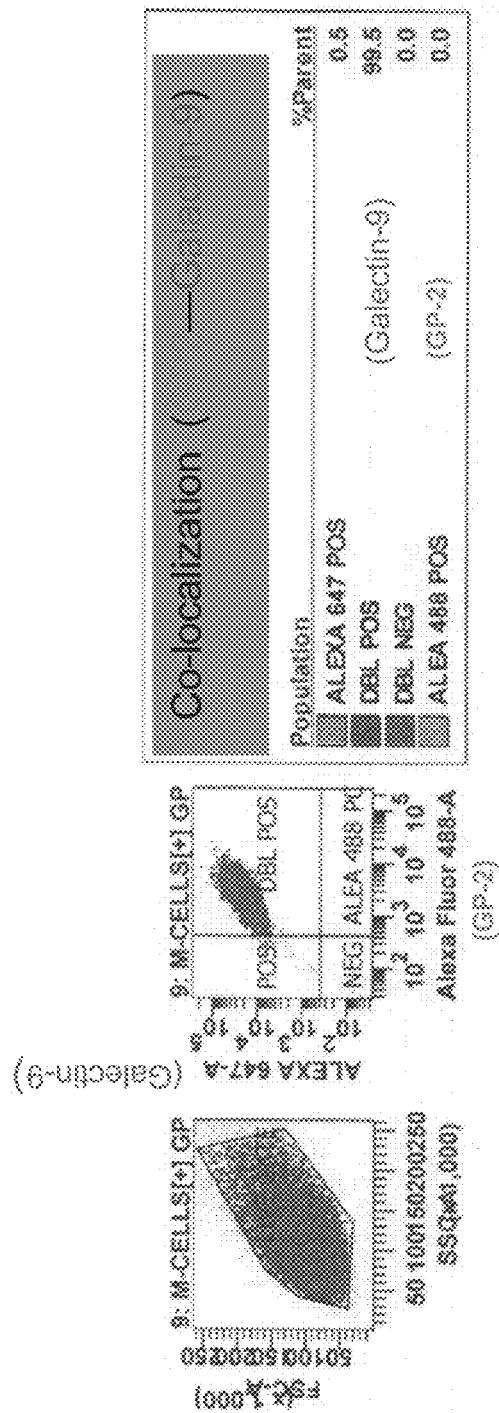
FIG. 5A is a diagram showing the results measured by a flow cytometer of the size of the cells which constitute the artificial skin sheet according to the present invention.
FIG. 5B is a diagram showing the fluorescence intensity in a case where the galectin-9 was stained by dark red fluorescence (ALEXA. 647) as shown in the vertical axis and the GP2 was stained by green fluorescence (ALEXA. 488) as shown in the horizontal axis.
FIG. 5C is a table showing the results of FIG. 5B.

In FIGS. 5A to 5C, the cells shown in FIGS. 1A and 1B were continued to be cultured until the $7^{th}$ day, and the intracellular binding of the formed cell sheet was decomposed by an enzymatic treatment. Subsequently, immunostaining was performed by using GP2 antibodies and the galectin-9 antibodies, and the amount of protein (GP2 and galectin-9) expressed inside a single cell was measured by a flow cytometry.

FIG. 5A shows the size of the cells by using the electrical resistance and such. It is observed from this figure that the measurement by flow cytometry was performed on the cells which were uniform in size.

The vertical axis (Y-axis) of FIG. 5B shows the intensity of fluorescence in a case in which the galectin-9 is stained with deep red fluorescence (ALEXA. 647), and the horizontal axis (X-axis) shows the intensity of fluorescence in a case in which GP2 is stained with green fluorescence (ALEXA. 488). FIG. 5C shows the results obtained by automatically calculating the measurement results of FIG. 5B with the software of the instruments.

In FIG. 5C, "ALEXA. 647 POS 0.5%" represents that the ratio of the cells in which only the galectin-9 was stained is 0.5%, and "DBL. POS 99.5%" represents that the ratio of the cells from which two colors were detected simultaneously is 99.5%. "DBL. NEG 0%" represents that the ratio of the cells which were stained by neither of two colors is 0%, and "ALEXA. 488 POS 0.0%" represents that the ratio of the cells in which only GP2 was stained is 0%.

From the results shown in FIGS. 5A to 5C, it is observed that the M cells constituting the artificial skin according to the present invention are uniform in size, and 99.5% of the cells express GP2 and galectin-9, while 0.5% of the cells express only galectin-9.

Figure 6:
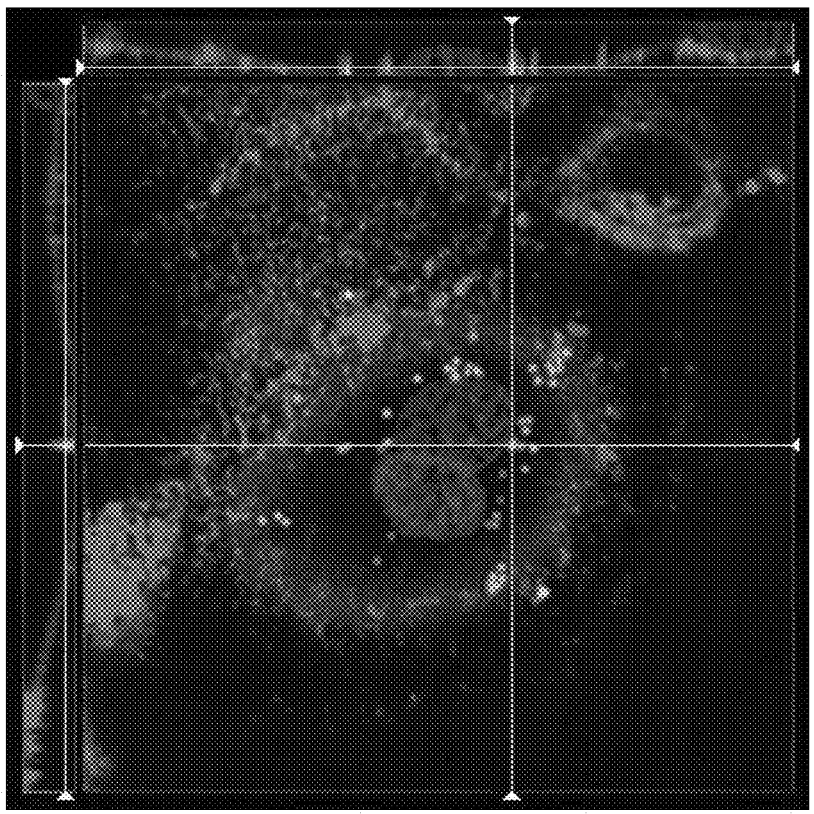
FIG. 6 is a microscope photograph showing a state in which foreign objects (beads) are taken into the cells constituting the artificial skin sheet according to the present invention.

FIG. 6 is a microscope photograph of the artificial skin according to the present invention obtained by adding polystyrene beads with a diameter of 1 μm to the top surface of the artificial skin and culturing for 20 hours under the condition of 37° C. and 5% $CO^2$. From this microscope photograph, it is observed that a large number of beads (foreign objects) were taken inside the cells. Therefore, it is presumed that the production of galectin-9 has increased due to stimulation by bead uptake.

FIG. 7 shows photographs of the artificial skin according to the present invention from the cultivation of the artificial skin to the formation of a sheet. The photographs of upper left, lower left and upper right, were taken from above, showing that the artificial skin sheet is floating in the cultivation container. The lower right photograph is a photograph showing the size of the artificial skin sheet with a ballpoint pen being used as a substitute for a scale.

The above-mentioned cultivation is performed first by adjusting the concentration of the M cells to $4 \times 10^5$ cell/ml, adding 15 ml of a cell solution with respect to 150 $cm^2$ of the cultivation container, replacing the culture solution with a new solution on the initial $4^{th}$ day, and again replacing the culture solution on the next $4^{th}$ day. At this point, it should be ensured that the cells have increased to fully cover the plastic surface.

If the cells have not sufficiently increased, the cultivation should be continued until the plastic surface is filled with the cells.

When the M cells fully cover the cultivation container, the culture solution is replaced with a culture solution with no serum component, and 150 μl of anti-LTβR antibodies are added to the culture solution. With the stimulation of these anti-LTβR antibodies, the GP2 inside the cells are moved to the intercellular junctions (tight junctions), and intercellular binding becomes strong. As a result, the formation of a large-sized cell sheet can be achieved.

Figure 8:
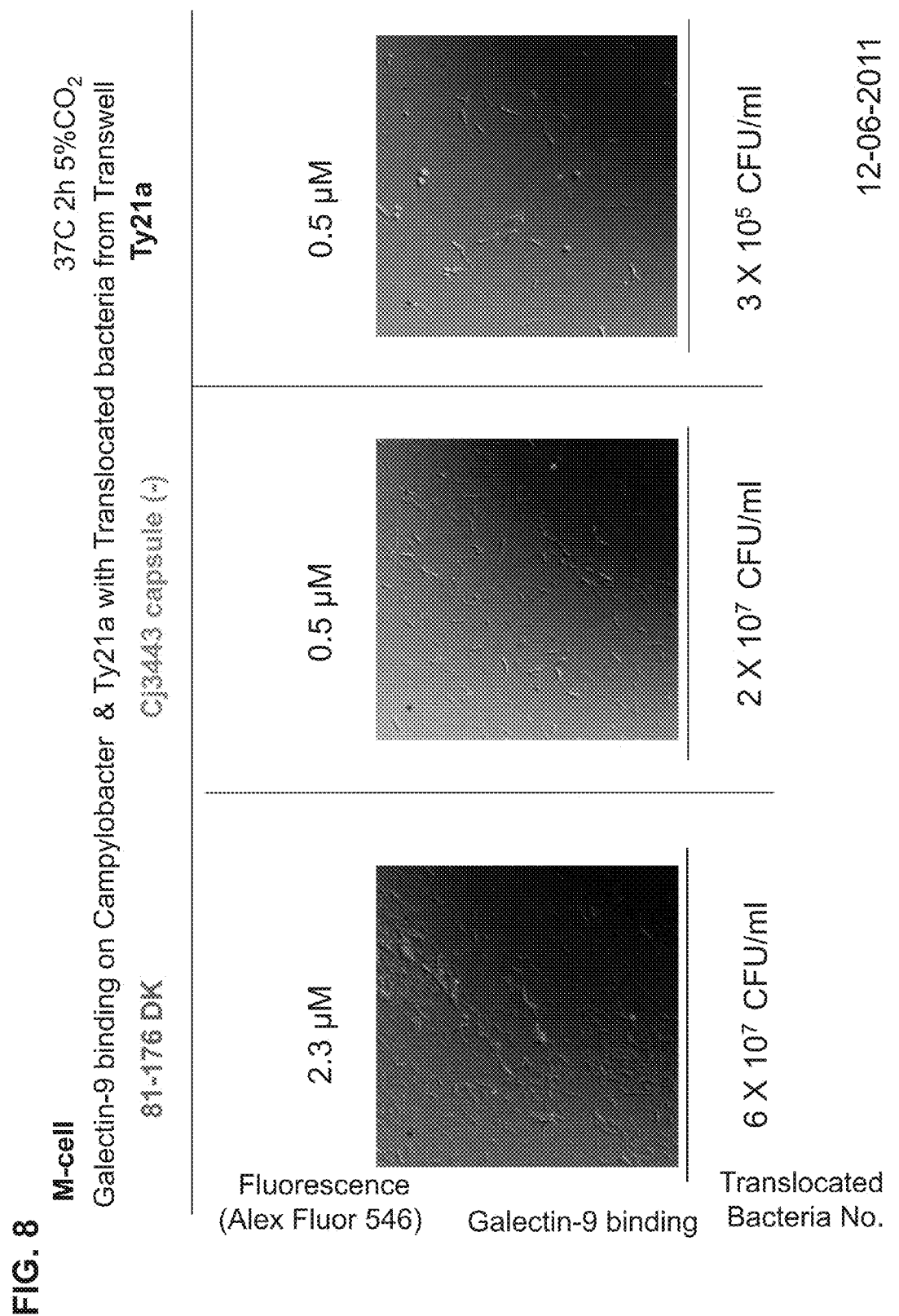
FIG. 8 is a microscope photograph showing the results of examining whether the galectin-9 is bound with bacteria which have passed through the M cells.
Figure 9:
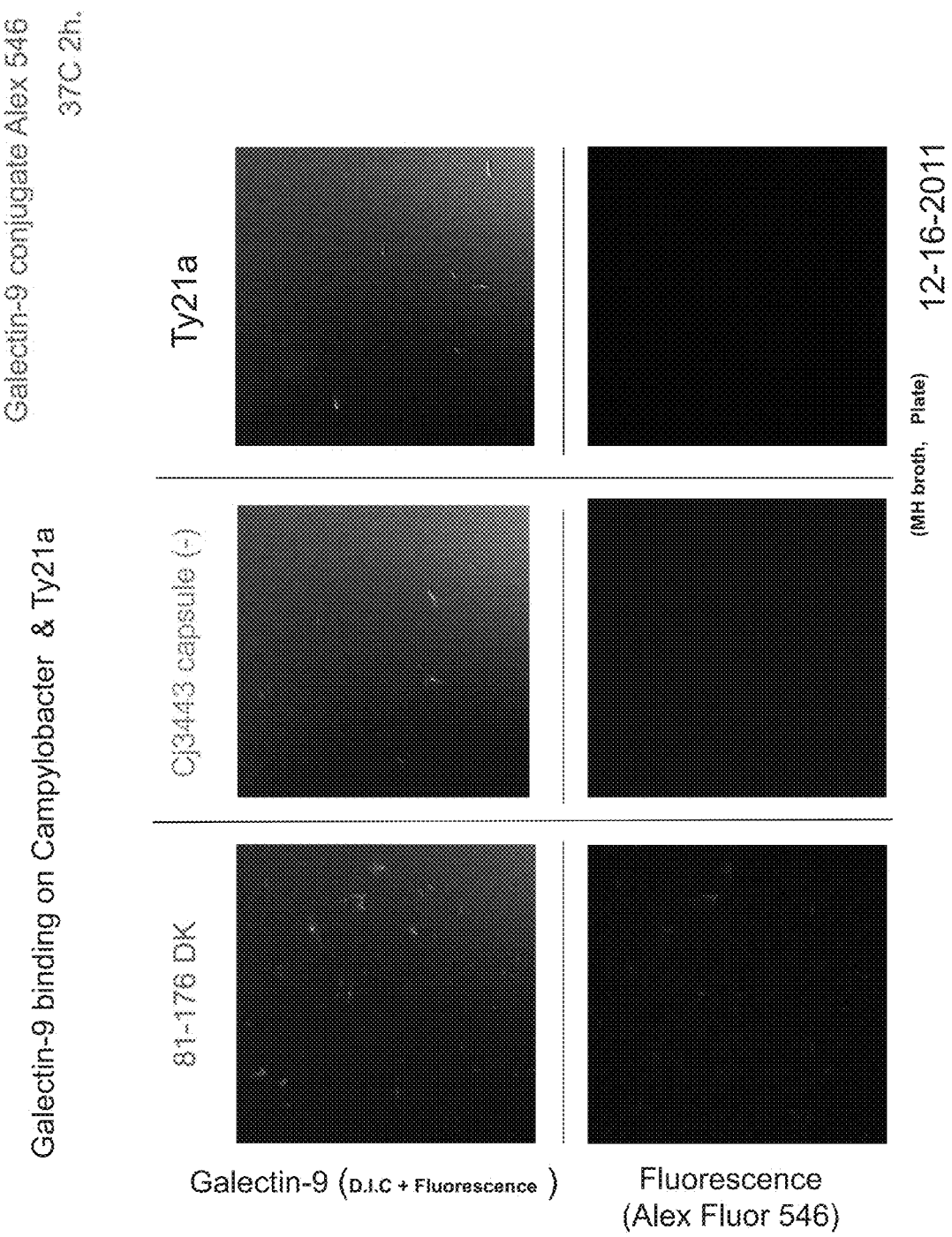
FIG. 9 is a microscope photograph showing the results of directly examining the binding of galectin-9 and bacteria in a test tube.
Figure 10:
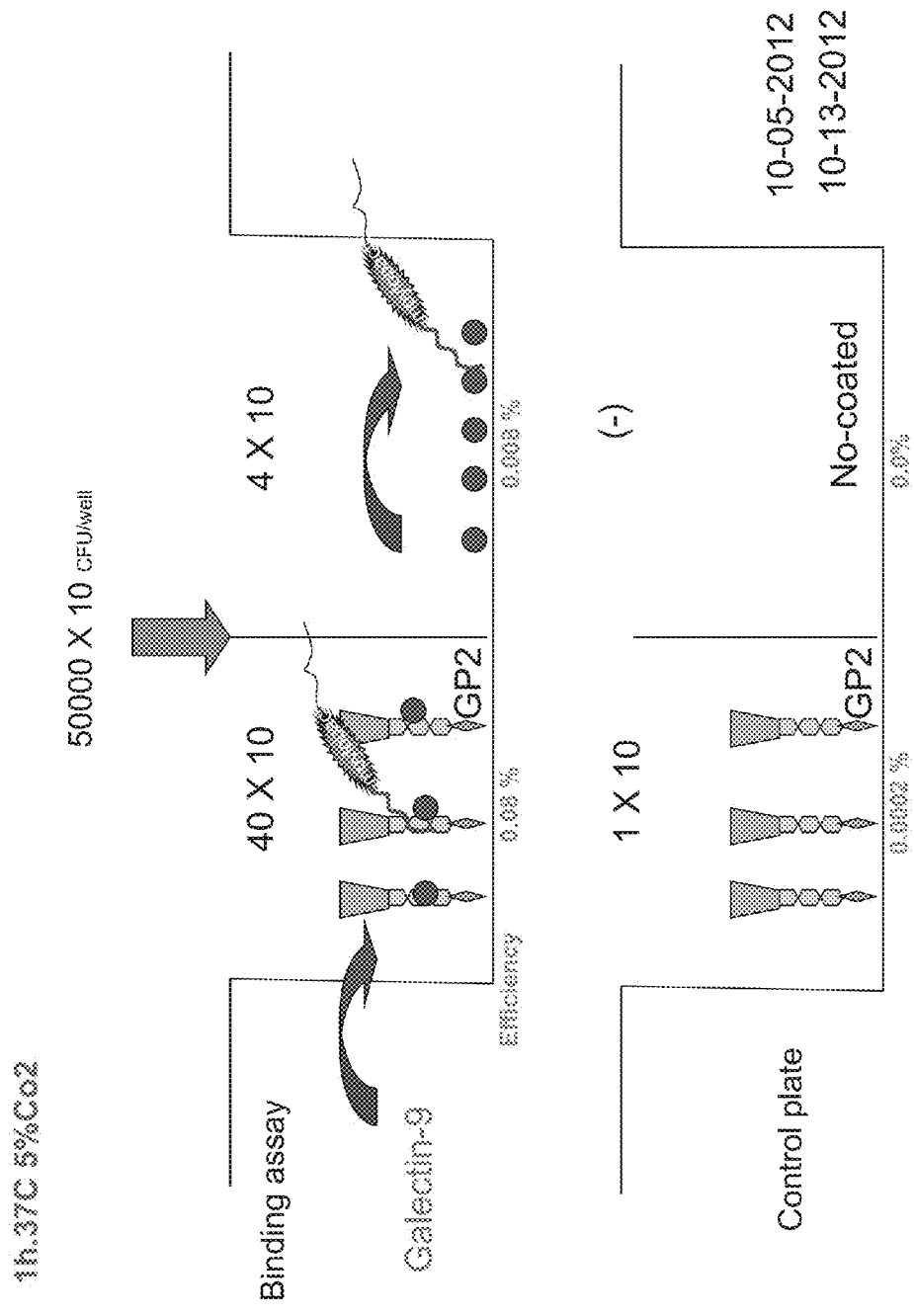
FIG. 10 is a diagram showing the number of bound bacteria (*C. jejuni* 81-176).
Figure 11:
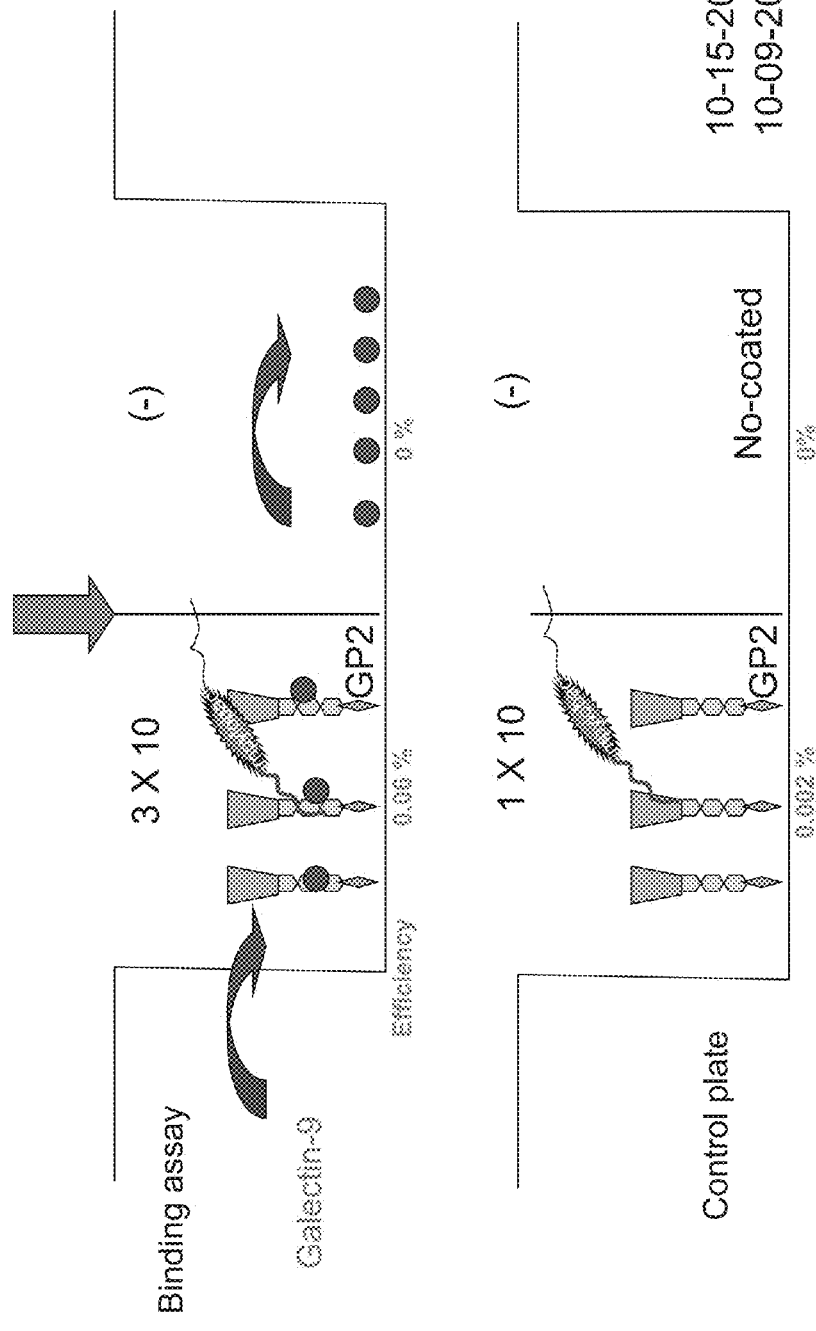
FIG. 11 is a diagram showing the number of bound bacteria (*C. jejuni* (cj3443)).
Figure 12:
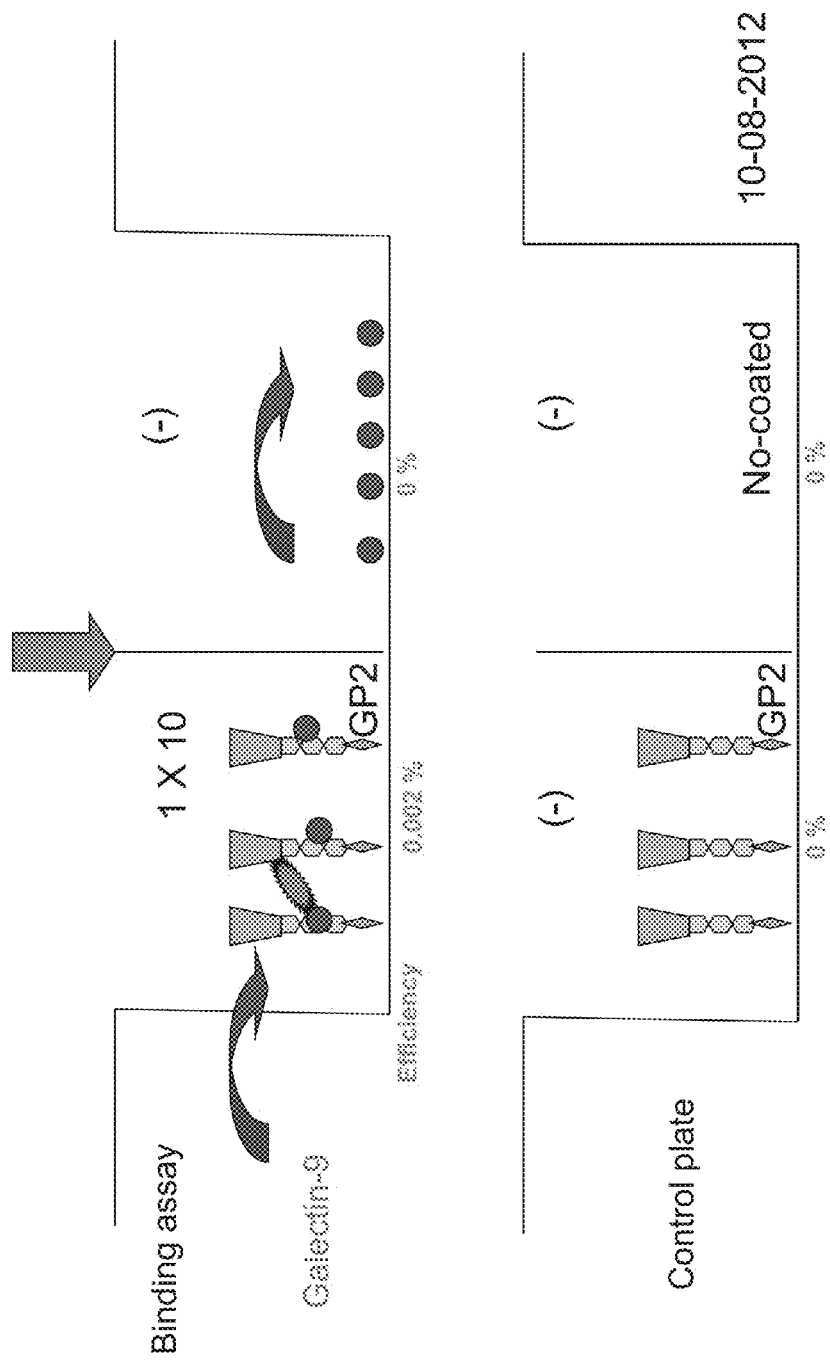
FIG. 12 is a diagram showing the number of bound bacteria (Ty21a).
Figure 13:
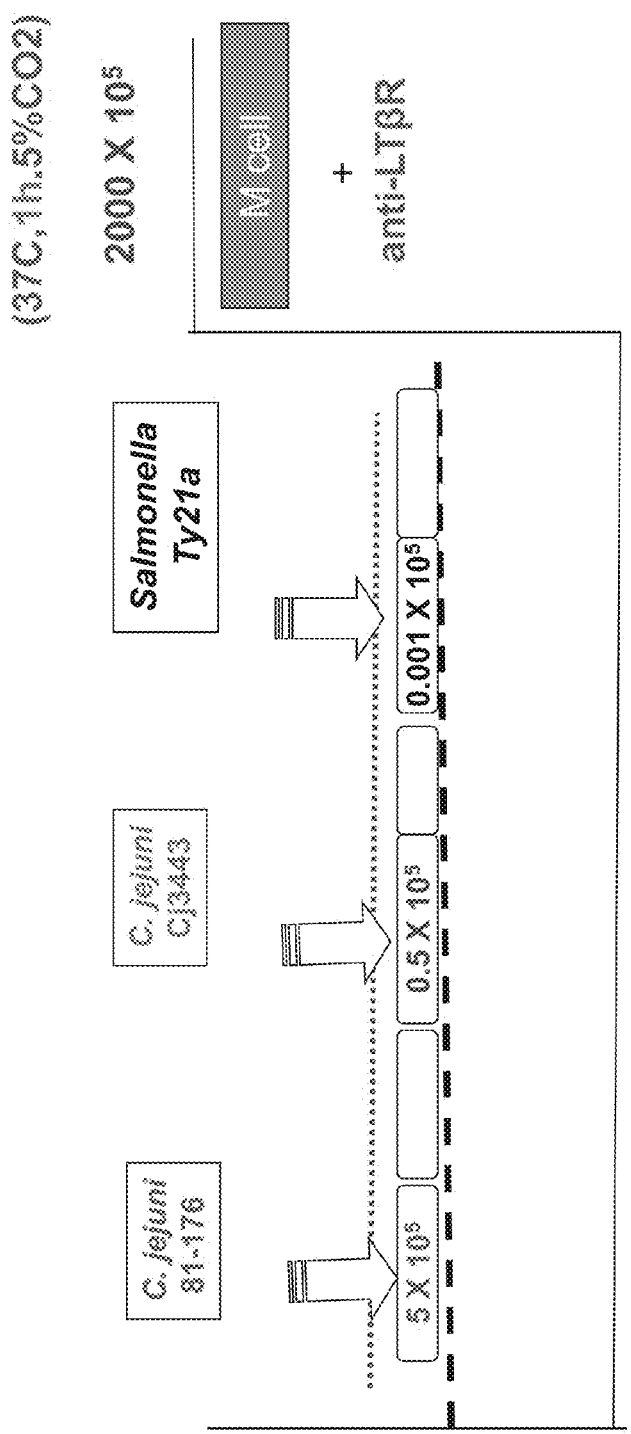
FIG. 13 is a diagram showing the number of each kind of bacteria entering into the M cells.

FIG. 8 is a photograph showing the results of examining how galectin-9 in the M cells constituting the cell sheet binds with bacteria.

81-176DK is a pathogen which causes human diarrhea and produces a lot of galactose. The flagella of this pathogen also have a component which binds with the galectin-9.

Cj 3443 capsule (–) is the same bacterium as 81-176DK, but it expresses only a small amount of galactose because of its structural deficiency.

Ty21a is one type of *salmonellas*, which does not express galactose on the cell surface.

From FIG. 8, it is observed that the galectin-9 binding with the bacterium which produces galactose is expressed on the surface or inside of the M cells.

FIG. 9 is a microscope photograph showing the results of directly examining the binding of the galectin-9 and the bacteria in a test tube. It is observed from these results that the binding ability of the galectin-9 differs depending on the type of the bacteria.

FIGS. 10 to 12 are diagrams showing the number of bound bacteria detected with the use of a culture method. In each diagram, the upper left drawing shows a commercially available plate (GA GENERIC ASSAYS GmbH; Germany) onto which recombinant GP2 was fixed and dried, and 20 μl (100 μg/ml) of recombinant galectin-9 (R&D; USA) was added and dried. In the upper right drawing, only galectin-9 was fixed. In the lower left drawing, only GP2 was fixed. The lower right figure shows a case in which neither of galectin-9 nor GP2 was fixed.

In FIG. 10, 500,000 counts of *C. jejuni* 81-176 (*Campylobacter jejuni* strain number; 81-176) were added to each plate, and shows how many among them adhered. In the case of fixing the GP2 and the galectin-9 to the plastic plate (upper left), 400 counts of the bacteria adhered. In the case of fixing only the galectin-9 (upper right), 40 counts of the bacteria adhered. In the case of fixing only the GP2 (lower left), 10 counts of the bacteria adhered. In the case of fixing none of the galectin-9 and the GP2 (lower right), 0 count of the bacteria adhered.

In FIG. 11, 600,000 counts of *C. jejuni* (cj3443) (*Campylobacter jejuni* strain number; cj3443) were added to each plate, and shows how many among them adhered. In the case of fixing the GP2 and the galectin-9 to the plastic plate (upper left), 20 counts of the bacteria adhered. In the case of fixing only the galectin-9 (upper right), 20 counts of the bacteria adhered. In the cases of fixing only the GP2 (lower left) and fixing none of the galectin-9 and the GP2 (lower right), 0 count of the bacteria adhered.

In FIG. 12, 500,000 counts of Ty21a (*Salmonella* strain number; Ty21a) were added to each plate, and shows how many among them adhered. In the case of fixing the GP2 and the galectin-9 to the plastic plate (upper left), 10 counts of the bacteria adhered. In the cases of fixing only the galectin-9 (upper right), fixing only the GP2 (lower left), and fixing none of the galectin-9 and the GP2 (lower right), 0 count of the bacteria adhered.

From FIGS. 10 to 12, it is observed that the number of bound bacteria differs depending on the type of the bacteria, and more of bacteria can be captured when the galectin-9 and the GP2 coexist than the case of fixing the galectin-9 only or the GP2 only.

FIG. 13 shows the number of bacteria entering into the M cells (in one hour). The bacteria entering into the M cells are discharged to the outside of the cells with the galectin-9 still being bound together.

The artificial skin according to the present invention can be utilized for a broad range of conditions such as atopic dermatitis, severe burns, and those caused by traffic accidents. Moreover, by freezing and storing the M cells, the artificial skin without transplant rejection can be cultured and obtained whenever necessary.

The invention claimed is:

1. An artificial skin sheet comprising:

microfold cells (M cells) in which the glycoprotein 2 (GP2) contained in the M cells is located in tight junctions between the cells after having moved to the tight junctions, and in which galectin-9 is expressed.

2. The artificial skin sheet according to claim 1, wherein the M cells are derived from CaCo-2 cells.

* * * * *